(12) United States Patent
Lechner

(10) Patent No.: US 11,021,818 B2
(45) Date of Patent: Jun. 1, 2021

(54) SEAMLESS COMPRESSION ARTICLE

(71) Applicant: JULIUS ZORN INC., Cuyahoga Falls, OH (US)

(72) Inventor: Siegfried Lechner, Schrobenhausen (DE)

(73) Assignee: JULIUS ZORN INC., Cuyahoga Falls, OH (US)

( * ) Notice: Subject to any disclaimer, the term of this patent is extended or adjusted under 35 U.S.C. 154(b) by 54 days.

(21) Appl. No.: 16/410,101

(22) Filed: May 13, 2019

(65) Prior Publication Data
US 2019/0350271 A1 Nov. 21, 2019

(30) Foreign Application Priority Data

May 17, 2018 (DE) ...................... 20 2018 102 766.2

(51) Int. Cl.
*D04B 1/26* (2006.01)
*A41B 11/00* (2006.01)
(Continued)

(52) U.S. Cl.
CPC ............ *D04B 1/265* (2013.01); *A41B 11/003* (2013.01); *A41B 11/005* (2013.01);
(Continued)

(58) Field of Classification Search
CPC . D04B 1/265; D04B 9/52; D04B 9/56; D04B 1/26; D04B 1/28; D04B 7/32;
(Continued)

(56) References Cited

U.S. PATENT DOCUMENTS

| 268,734 | A | * | 12/1882 | Scott | ........................ | D04B 1/26 |
| | | | | | | 66/188 |
| 1,075,864 | A | * | 10/1913 | Scott | ...................... | A41B 11/00 |
| | | | | | | 2/239 |

(Continued)

FOREIGN PATENT DOCUMENTS

| DE | 705704 C | 5/1941 |
| DE | 1610501 A1 | 7/1971 |

(Continued)

OTHER PUBLICATIONS

European Search Report dated May 29, 2020, for European Patent Application No. 19164052.
(Continued)

*Primary Examiner* — Danny Worrell
(74) *Attorney, Agent, or Firm* — Paul D. Bianco; Gary S. Winer; Fielt Intellectual Property Law

(57) ABSTRACT

A seamless compression article is knitted on a flatbed knitting machine having a front needle bed and a rear needle bed opposite thereto. The compression article includes a base structure of at least one weft thread, at least one elastic warp thread inserted or knitted therein, and at least one tubular or pocket-like receptacle extending along a longitudinal direction for at least one finger or at least one toe of a wearer of the compression article and can be placed on a body extremity of the wearer extending in the longitudinal direction. The receptacle includes a number of rib-like elevations, which run substantially parallel to each other and along the longitudinal direction of the corresponding receptacle. Putting on the compression article can thereby be facilitated.

19 Claims, 6 Drawing Sheets

(51) Int. Cl.
*A41D 19/00* (2006.01)
*A61F 13/08* (2006.01)
*A61F 13/10* (2006.01)
*D04B 7/34* (2006.01)

(52) U.S. Cl.
CPC .......... *A41D 19/0006* (2013.01); *A61F 13/08* (2013.01); *A61F 13/105* (2013.01); *D04B 7/34* (2013.01); *A41B 2500/10* (2013.01); *A41D 2400/32* (2013.01); *D10B 2501/041* (2013.01); *D10B 2501/043* (2013.01)

(58) Field of Classification Search
CPC .... D04B 7/34; D04B 9/50; D04B 9/54; A61F 13/08; A41B 11/003; A41B 11/004
See application file for complete search history.

(56) References Cited

U.S. PATENT DOCUMENTS

| | | | | |
|---|---|---|---|---|
| 1,715,657 A | * | 6/1929 | Holden | D04B 1/26 66/178 R |
| 1,941,508 A | | 1/1934 | Zwicker | |
| 2,252,768 A | * | 8/1941 | Houseman | D04B 9/10 66/185 |
| 3,386,270 A | | 6/1968 | Simmons | |
| 3,905,212 A | | 9/1975 | Bounous | |
| 4,149,274 A | * | 4/1979 | Garrou | A41B 11/02 2/239 |
| 7,434,423 B1 | * | 10/2008 | Reid, Jr. | A61F 13/08 66/178 A |
| 7,587,915 B2 | * | 9/2009 | Kaneda | D04B 1/26 2/239 |
| 2006/0021390 A1 | | 2/2006 | Gebel et al. | |
| 2011/0092872 A1 | | 4/2011 | Christiansen | |
| 2017/0335495 A1 | * | 11/2017 | Kostian | D04B 1/102 |

FOREIGN PATENT DOCUMENTS

| | | |
|---|---|---|
| DE | 10084580 C2 | 10/2003 |
| DE | 102004036344 A1 | 3/2006 |
| DE | 102007063148 A1 | 7/2009 |
| DE | 202012004652 U1 | 8/2013 |
| EP | 1679012 A1 | 7/2006 |
| EP | 2314260 A1 | 4/2011 |
| WO | 2012/067645 A1 | 5/2012 |
| WO | 2013/123038 A1 | 8/2013 |

OTHER PUBLICATIONS

Result of Examination Report for German Application No. DE 20 2018 102 766.2 filed May 17, 2018.

* cited by examiner

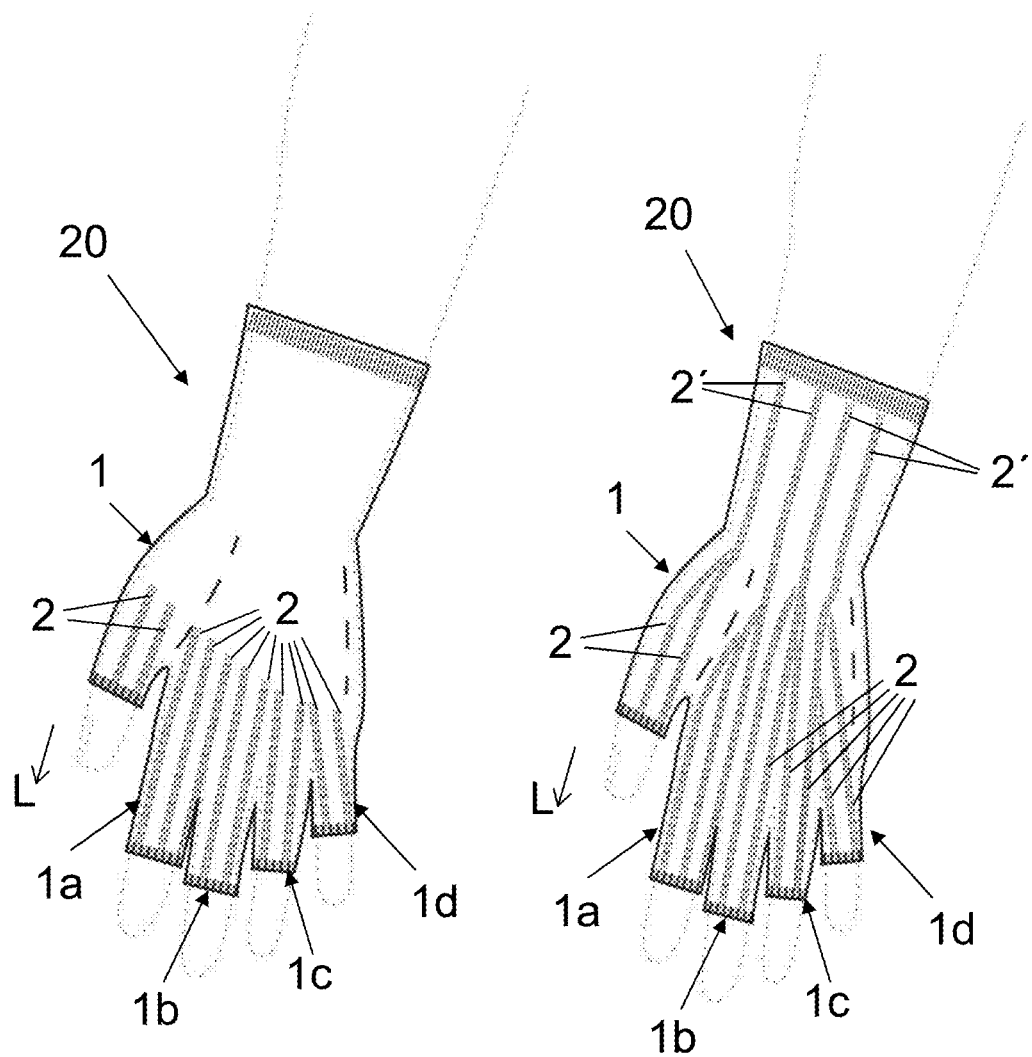

SEAMLESS COMPRESSION ARTICLE

FIELD OF THE DISCLOSURE

The disclosure relates to a seamless compression article knitted on a flatbed knitting machine.

BACKGROUND

A seamless compression glove that is knitted on a flatbed knitting machine having a front and rear needle bed is known from EP 1 679 012 B1. The compression glove consists of a base structure, which is knitted either from a fingertip to the opening of the glove or from the opening to the fingertip, the base structure being knitted based on a rib knit structure, using a stretch-elastic yarn inserted into the base structure in a stretched state. Knitting preferably occurs from the fingertip to the opening, in which case the stretch-elastic yarn is knotted at least at a site at which knitting of the finger begins, as well as at an interdigital fold in order to prevent ejection of the stretch-elastic yarn. A front part and a rear part of each finger are then knitted by rib knitting of high stitch density so that a flat interstice is formed at each interdigital fold. The known compression glove is characterized by a high support effect (i.e., by a high compression pressure that the glove exerts on the hand of a wearer), and can therefore be used for compression therapy, for example, for treatment of lymphatic insufficiencies in the hand.

Owing to its high support performance, which is essentially ensured by the stretch-elastic yarn incorporated into the base structure, the known compression glove is difficult to put on. It is difficult, especially in the finger area, for a patient suffering from lymphatic insufficiency to pull the narrow compressing glove over the fingers.

SUMMARY

Consequently, one aspect of the disclosure relates to a compression article knitted seamlessly on a flatbed knitting machine, such as a compression glove, a compression sock or a compression lining, which has at least one tubular or pocket-like receptacle for at least one finger or at least one toe of a wearer of the compression article, which can be put on more easily, has high support performance, and can exert a high and uniform compression pressure on the body extremity of the wearer on which the compression article is placed.

Exemplary embodiments of a compression article are disclosed herein.

In one embodiment, the compression article knitted seamlessly on a flatbed knitting machine having a front and rear needle bed has at least one tubular or pocket-like receptacle extending in a longitudinal direction for at least one finger or at least one toe of a wearer of the compression article and can be positioned on a body extremity of the wearer extending at least essentially in a longitudinal direction, for example, a hand or foot. Putting on the compression article is facilitated according to the disclosure in that the receptacle or each receptacle includes a number of rib-like elevations that run at least essentially parallel to each other and along the longitudinal direction of the corresponding receptacle.

It has been shown that known seamless compression articles, especially the compression glove described in the background, which are knitted on a flatbed knitting machine with incorporation of an elastic warp thread into a base structure, are therefore difficult to put on because they have a high extensibility, i.e., high stretchability in the longitudinal direction. The extensibility is caused, on the one hand, by the design of the base structure and, on the other hand, by the use of an elastic weft thread, from which the base structure is knitted. Use of an elastic weft thread is useful in producing high support performance and a high compression effect.

The disclosure is based on the finding that the high extensibility of the known compression articles knitted seamlessly on a flatbed knitting machine can be reduced if a number of rib-like elevations that run parallel to each other and extend along the longitudinal direction of the corresponding receptacle are knitted into the base structure at least in the area of the receptacle or each receptacle of the compression article, which is provided to accommodate at least one finger or toe of the wearer. The rib-like elevations preferably protrude above the base structure on the outer side. The rib-like elevations that protrude above the base structure are then to be distinguished from the ribs that result during knitting of the base structure based on a rib knitting technique or rib knitting pattern and extend over the entire surface of the base structure knitted in the form of a rib knitting pattern. The base structure of the compression article according to the disclosure can therefore also be knitted with a rib knitting technique or with a rib knitting pattern, but then also has a number of rib-like elevations that preferably protrude above the base structure on the outer side in addition to the rib pattern of the base structure formed by the rib knitting technique, which extends over the entire surface of the base structure, in the area of the receptacle or each receptacle for at least one finger or toe.

The compression article according to the disclosure advantageously consists of a base structure with an inner side facing a body extremity during wearing and an outer side opposite the inner side. The base structure is then knitted along a wale direction and has courses running across the wale direction. When the compression article is positioned on a body extremity of a wearer, the wale direction then runs at least essentially along the longitudinal direction of the body extremity. In particular, the wale direction runs in the region of the receptacle or each receptacle of the compression article that is provided to accommodate at least one finger or toe of the wearer along the longitudinal direction of the corresponding receptacle.

Depending on the extent of the receptacle across the longitudinal direction, a receptacle can be provided to accommodate only one finger or toe or also to accommodate several fingers or toes.

Formation of the rib-like elevations so that they protrude above the base structure on the outer side of the compression article, on the one hand, facilitates lay-up of the compression article on a flatbed knitting machine and also prevents a wearer from snagging a fingernail or toenail on the rib-like elevations when the compression article is put on.

It has been shown that ease of use of the compression article according to the disclosure has already been provided by forming at least two rib-like elevations on each tubular or pocket-like receptacle. Depending on the extent of the tubular or pocket-like receptacles, up to 30 rib-like elevations can be knitted on each receptacle. Each receptacle preferably has between three and seven rib-like elevations.

The rib-like elevations preferably extend over at least three stitches in each course of the base structure.

To achieve a high compression effect, it is advantageous if an elastic warp thread is inserted or incorporated into the base structure knitted from a weft thread. A particularly high compression effect can then be achieved if an elastic warp thread is inserted or incorporated into each course of the base structure.

The elevations extending along the longitudinal direction of the corresponding receptacle for a finger or a toe are arranged at a predetermined spacing relative to each other in the base structure lying in the course direction. At least two stitches of the weft thread from which the base structure is knitted preferably lie between two consecutive elevations in a course. The spacing between adjacent elevations in a course, however, can also extend over more than two stitches of the base structure, for example, over five to 10 stitches.

If a more limited compression effect is required, an elastic warp thread can also be provided only in every second course. It is also possible to not introduce any warp threads in several consecutive courses in pressure-reduced areas of the base structure that extend over more than two consecutive courses in the wale direction.

Formation of the rib-like elevations in the base structure advantageously occurs through float loops of the weft thread of the base structure and/or by formation of tuck loops. In a preferred practical example of the compression article in which a warp thread is incorporated into the base structure, the warp thread can then be incorporated as a tuck in the base structure between two consecutive elevations in the direction of the courses. The warp thread is then preferably incorporated as a tuck in the base structure between two consecutive elevations in the course direction in every second stitch of the base structure.

A delimitation of the elevations protruding above the base structure can be formed by forming two consecutive tuck stitches of the warp thread in the courses in the edge areas of the elevations.

To minimize the extensibility of the receptacles of the compression article provided to accommodate at least one finger or toe, it is advantageous if the elevations of the receptacle or each receptacle extend in the longitudinal direction at least essentially over the entire extent of the receptacle in the longitudinal direction.

In order to guarantee the highest possible compression effect of the compression article outside of the area in which the receptacles are found, it is advantageous if no rib-like elevations are present according to the disclosure in the areas outside the receptacles. Especially in custom-made compression articles according to the disclosure, it is also simpler to lay up the compression articles if no rib-like elevations are present outside the receptacles.

The compression article according to the disclosure is knitted on a flatbed knitting machine having a front and rear needle bed, in which case the base structure of the compression article therefore acquires a front layer that is knitted on the front needle bed and a rear layer that is knitted on the rear needle bed and is thereby formed in a tubular shape. The front and rear layers of the compression article are then seamlessly joined to each other, i.e., knitted to each other. The front and rear layers of the base structure then contain a weft thread, in which the weft thread forms floats to form the rib-like elevations and the sites at which the weft thread floats are arranged offset to each other by at least one stitch, preferably by one or two stitches in consecutive courses in the wale direction. The width of the rib-like elevations (i.e., their extent in the course direction) can be defined by the number of stitches by which offsetting of the floats of the weft thread occurs.

BRIEF DESCRIPTION OF THE DRAWINGS

These advantages and additional advantages as well as advantageous features of the disclosure will become apparent from the practical examples described below with reference to the accompanying drawings. In the drawings:

FIGS. 4A and 4B: show compression articles according to the disclosure designed as a compression glove, in which a first embodiment of a compression glove is shown in FIG. 4A, in which rib-like elevations are provided only in the area of the finger receptacles and in FIG. 4B a second embodiment of a compression glove is shown in which rib-like elevations according to the disclosure are provided over the entire length of the sleeve;

DETAILED DESCRIPTION

Figures 3A, 3B:
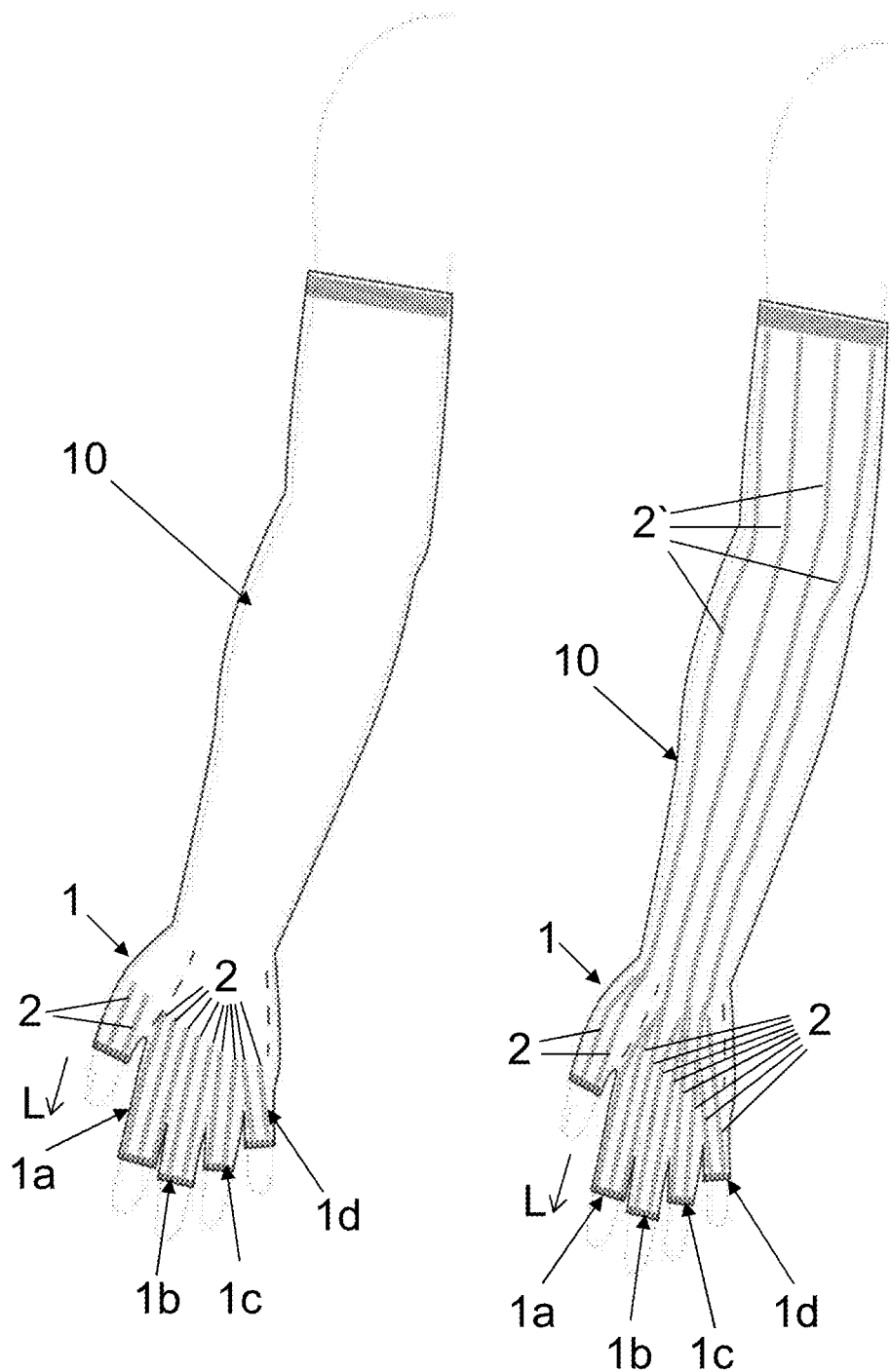
FIGS. 3A and 3B: show compression articles according to the disclosure designed as compression sleeves, in which a first embodiment of a compression sleeve is shown in FIG. 3A, in which rib-like elevations are only provided in the area of the finger receptacles, and in FIG. 3B a second embodiment of a compression sleeve is shown in which rib-like elevations according to the disclosure are provided over the entire length of the sleeve.

The practical examples of a compression article according to the disclosure shown in FIGS. 3A and 3B and formed as compression sleeves have five receptacles 1, 1a, 1b, 1c, 1d to accommodate five fingers of a hand of a wearer of the compression sleeve, one receptacle 1 being provided to accommodate the thumb and the other receptacles 1a-1d to accommodate the other fingers of the hand. The receptacles, which are marked subsequently with reference number 1, extend along a longitudinal direction L, which corresponds to the longitudinal direction of the corresponding finger of the hand. The finger receptacles 1 drawn here in the practical example are open and have a cuff at the open end. However, in the context of the disclosure the receptacles 1 could also be designed closed, i.e., with a closed fingertip. The cuff is omitted in this embodiment.

In the two practical examples of a compression article according to the disclosure shown in FIGS. 3A and 3B in the form of a compression sleeve, several rib-like elevations 2 are provided in the area of receptacles 1, which run at least essentially parallel to each other and extend along the longitudinal direction L of the corresponding receptacle 1. A number of rib-like elevations 2 are then arranged on each receptacle 1, in which the rib-like elevations 2 extend at least essentially over the entire extent of the corresponding receptacle 1 in its longitudinal direction L. In the practical example of a compression sleeve depicted in FIG. 3A no elevations 2 are provided outside the areas of receptacles 1. On the other hand, in the practical example of a compression sleeve depicted in FIG. 3B, rib-like elevations 2' are also provided in the areas outside receptacles 1, which extend at least essentially along the longitudinal direction of the sleeve and run at least roughly parallel to each other.

The rib-like elevations 2, 2' then reduce the extensibility of the compression article in the area of receptacles 1 and in the entire area of the compression article and in so doing facilitate putting on the compression sleeve, especially pulling the receptacles 1 over the fingers of the hand of the wearer or over the entire hand and arm of the wearer.

The compression sleeves depicted in FIGS. 3A and 3B, like all other embodiments of the compression article according to the disclosure, are knitted seamlessly on a flatbed knitting machine having a front and opposite rear needle bed, in which the tubular or pocket-like receptacles 1 that are provided to accommodate at least one finger or one toe of the wearer and that extend along the longitudinal direction L are knitted seamlessly in the compression article.

The knit from which the compression articles according to the disclosure can be produced comprises a base structure from a weft thread with an inner side facing a body extremity when the compression article is worn on an extremity and an outer side opposite the inner side, the base structure being knitted along a wale direction and having courses running across the wale direction.

Figure 1:
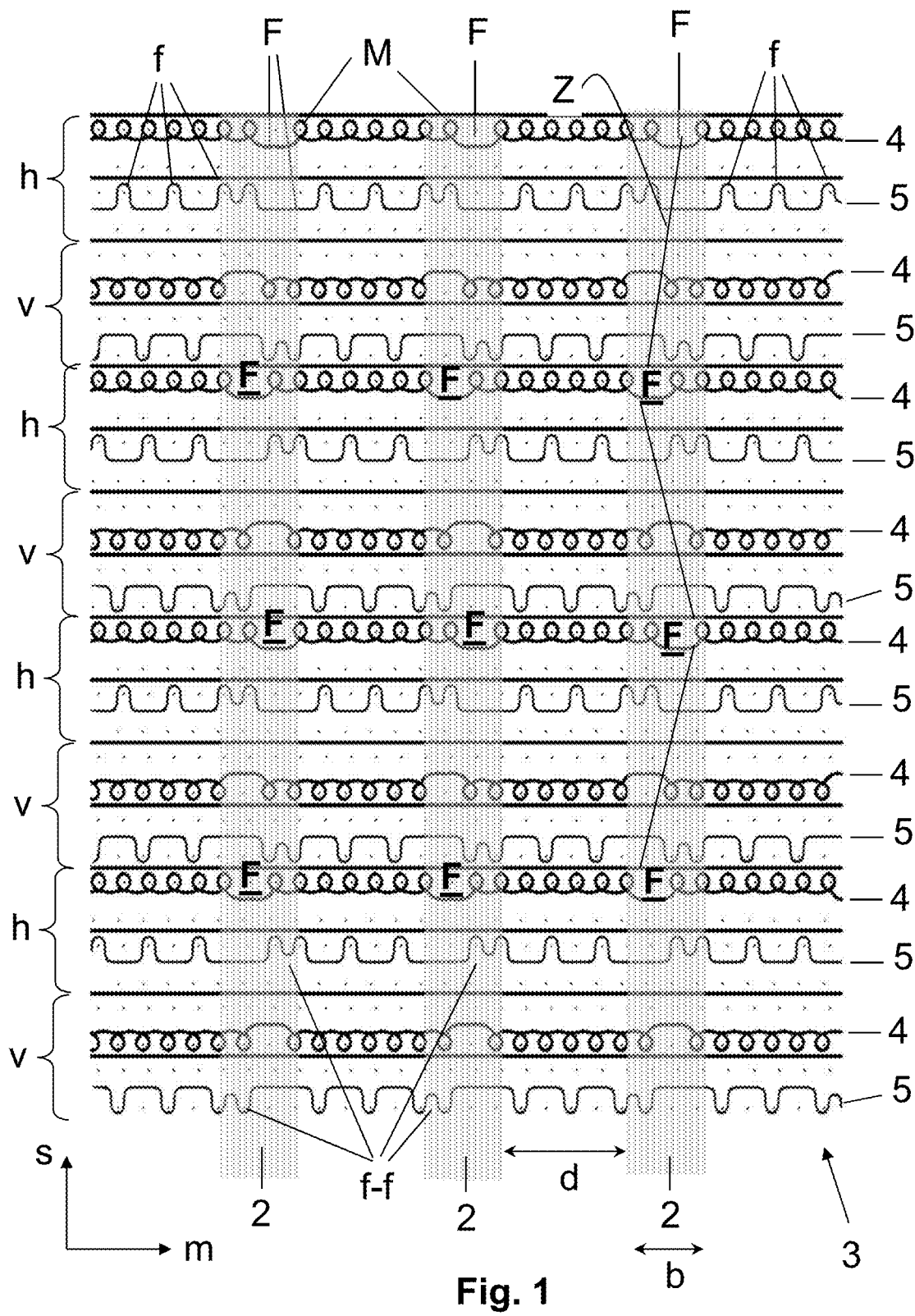
FIG. 1: shows a schematic depiction of a knitting pattern of a first embodiment of a knit from which at least a partial area of the compression article according to the disclosure can be produced.
Figures 2A, 2B:
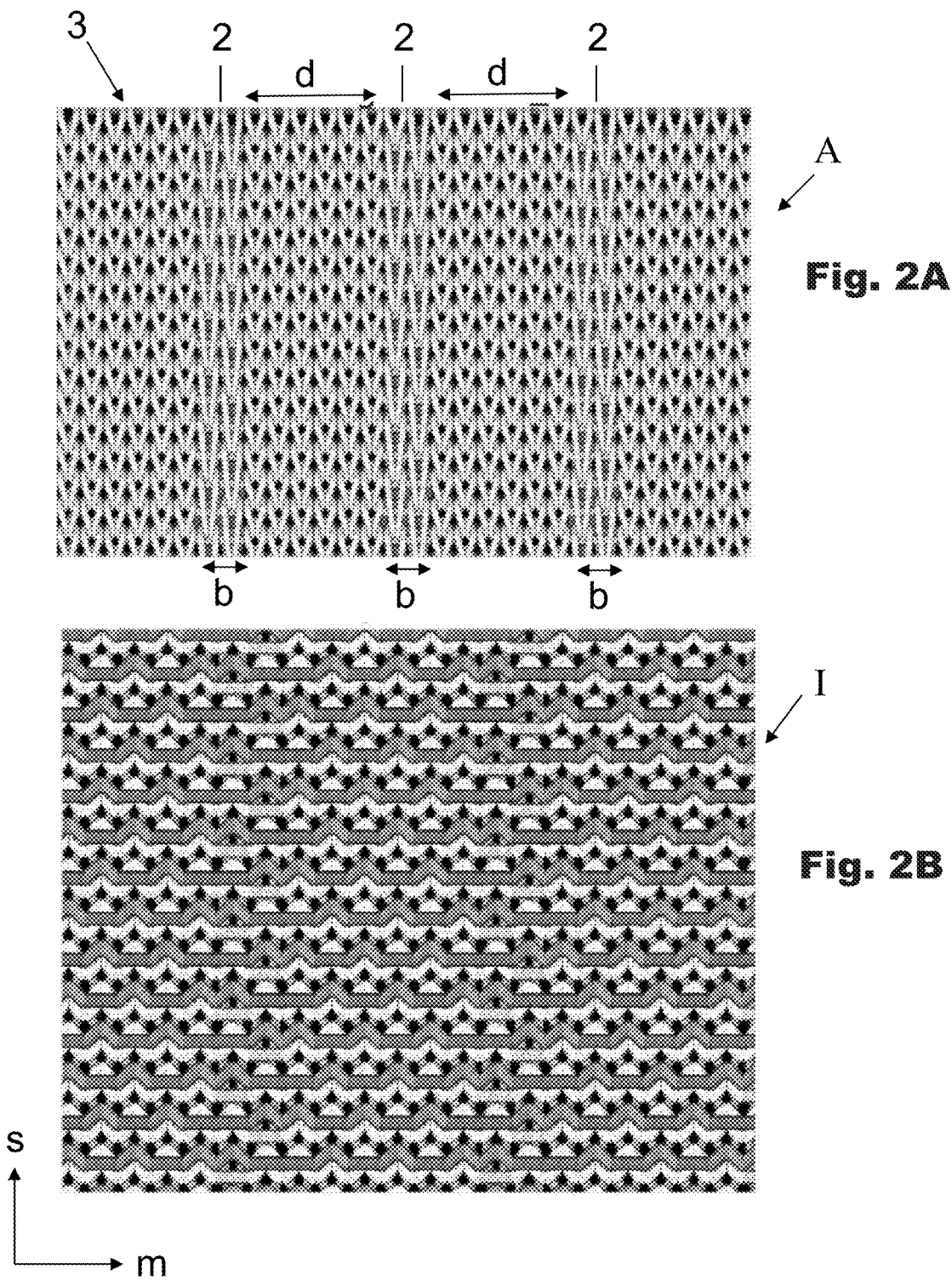
FIGS. 2A and 2B: show the outer side (FIG. 2A) and the inner side (FIG. 2B) of the preferred knit for production of a compression article according to the disclosure.

A preferred knit is depicted in FIG. 1 and FIGS. 2A and 3B, from which at least the receptacles 1 of the compression article according to the disclosure can be produced.

It is apparent from the knit pattern of FIG. 1 that the knit contains a front layer v, which is knitted on the front needle bed of the flatbed knitting machine, and a rear layer h, which is knitted on the rear needle bed. The courses of the front layer v and the rear layer h in FIG. 1 are shown one above the other along the wale direction s. The design of the base structure of the front layer v and the rear layer h with the stitches M of the base structure running in the courses m is apparent from FIG. 1.

The base structure is then formed from a weft thread 4, which is knitted, for example, in a right-left knit or a 1:1 weave to form the base structure on the flatbed knitting machine. The base structure in the practical example depicted in FIG. 1 is designed as a right-left knit. The weft thread 4 can be an elastic or also an at least largely inelastic weft thread. Use of an elastic weft thread is to be preferred to form a high compression effect. If an elastic weft thread 4 is used, it can be a wrapped yarn with an elastic core thread.

In the preferred practical example of a knit appropriate for production of the compression article according to the disclosure depicted in FIG. 1 an elastic warp thread 5 is incorporated into each course m of the base structure formed from the weft thread 4. The elastic warp thread 5 can be a wrapped yarn with a highly elastic core thread or a spandex or rubber thread. The core thread or the entire warp thread advantageously has a thickness in the range of 200 to 1500 dtex. The warp thread 5 is then generally (much) thicker than the weft thread 4.

The rib-like elevations 2, which are provided at least in the area of receptacle 1 of the compression article according to the disclosure, are formed by floats F of the weft thread 4 in the courses m of the base structure. The elevations 2 at least essentially parallel to each other and arranged at a predetermined spacing d from each other in the course direction are shown in the knit pattern of FIG. 1 in a gray line field. The extent of the elevations 2 in the course direction m, i.e., their width b, is then obtained by the layer of the floats F of the weft thread 4, each of which are shown in the knit pattern of FIG. 1 with reference letter F. The sites at which the weft thread 4 forms floats F are arranged offset to each other by at least one stitch in the consecutive (or overlapping) courses m in the wale direction s in the front layer v and the rear layer a. In the knit pattern depicted in FIG. 1 the sites at which the weft thread 4 forms floats F in the front layer v and rear layer h are arranged offset to each other by one stitch. An interconnection Z of float sites F in the front layer v and rear layer h therefore forms a zig-zag line offset by one stitch and the edges of this zig-zag line in the courses m represent the lateral limits of elevations 2.

A predetermined number of stitches M of weft thread 4 are formed in course direction m between two consecutive elevations 2. The number of stitches M that are found between two elevations 2 adjacent in the course direction m, establishes the spacing d of the adjacent elevations 2 in the course direction m. At least two and preferably more than five stitches M preferably lie between two elevations 2 adjacent in the course direction. In the practical example depicted in FIG. 1 six stitches M of the weft thread 4 lie between elevations 2 adjacent in course direction m.

As is apparent from the knit pattern in FIG. 1 that a warp thread 5 is incorporated into each course m. The warp thread 5 then forms tuck loops f. In the edge areas of elevations 2, in particular, the warp thread forms two immediately consecutive tuck loops f-f in the courses m. In the areas between two adjacent elevations 2 in a course the warp thread 5 is inserted into the base structure formed by the weft thread 4 alternating as a tuck loop f and a float. By forming a double tuck loop f-f in the edge area of elevations 2, the base structure formed from the weft thread 4 is pulled together in the area of elevations 2, in which the weft thread 4 forms a float F so that an elevation 2 protruding above the other area of the base structure is formed.

Figure 6:
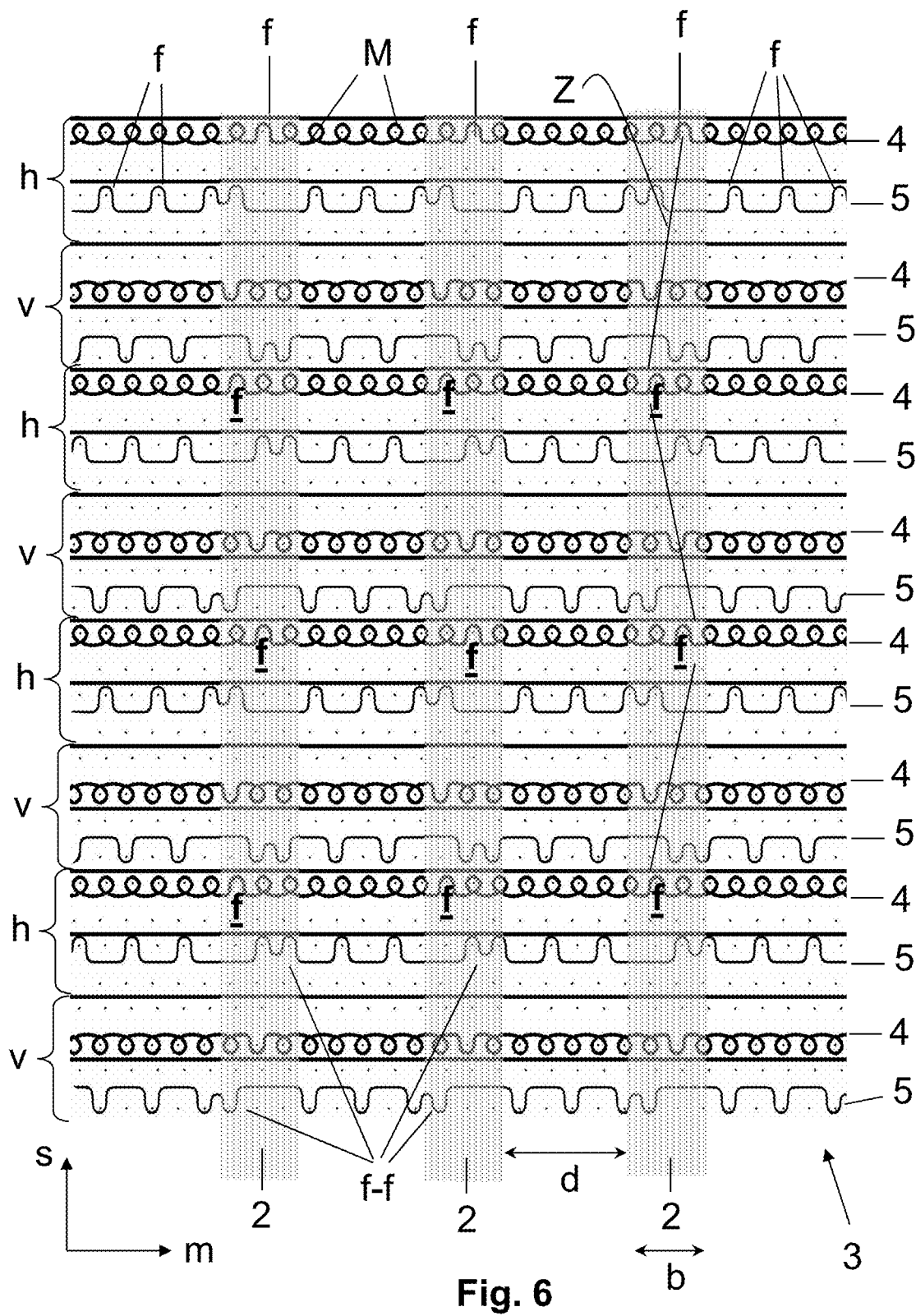
FIG. 6: shows a schematic of a knitting pattern of another embodiment of a knit from which at least a partial area of the compression article according to the disclosure can be produced.

Another embodiment of a knit is shown in FIG. 6 from which at least the areas of the receptacles 1 of the compression article according to the disclosure can be produced. This embodiment differs from the knit depicted in FIG. 1 in that the elevations 2 are formed by forming tuck loops f through the weft thread 4. For this purpose, tuck loops f are formed instead of floats at the sites at which the weft thread 4 forms floats F in the embodiment of FIG. 1. At the sites of tuck loop f, the weft thread 4, as in the floats F of the embodiment of FIG. 1, does not form any stitches through which the elevations 2 are formed.

A compression article according to the disclosure is preferably knitted from the knit schematically depicted in FIG. 1 or FIG. 6 so that the rib-like elevations 2 protruding above the base structure come to lie on the outer side of the compression article that faces away from the body extremity when placed on the extremity.

The outer side A and the inner side I of the knit of FIG. 1 are shown in FIGS. 2A and 2B, FIG. 2A showing the outer side A and FIG. 2B the inner side I. The elevations 2 that extend in the longitudinal direction L and in the course direction m at spacing d and that have a width b are apparent from FIG. 2a. The elevations 2 then protrude above the base structure and thus form rib-like elevations 2. The elevations 2 do not appear on the inner side I of the knit. This has an advantage in that the elevations 2 do not interfere when the compression article is put on and the wearer of the compression article cannot snag a fingernail or toenail on the elevations 2.

Additional practical examples of compression articles according to the disclosure are shown in FIGS. 4A and 4B and FIGS. 5A and 5B. FIGS. 4A and 4B show two compression articles formed as compression gloves, in which rib-like elevations 2 are only provided in the area of the receptacles 1 for the fingers of the wearer in the compression glove depicted in FIG. 4A, whereas in the practical example of the compression glove depicted in FIG. 4B rib-like elevations 2' are also arranged in the area outside the receptacles 1.

Figures 5A, 5B:
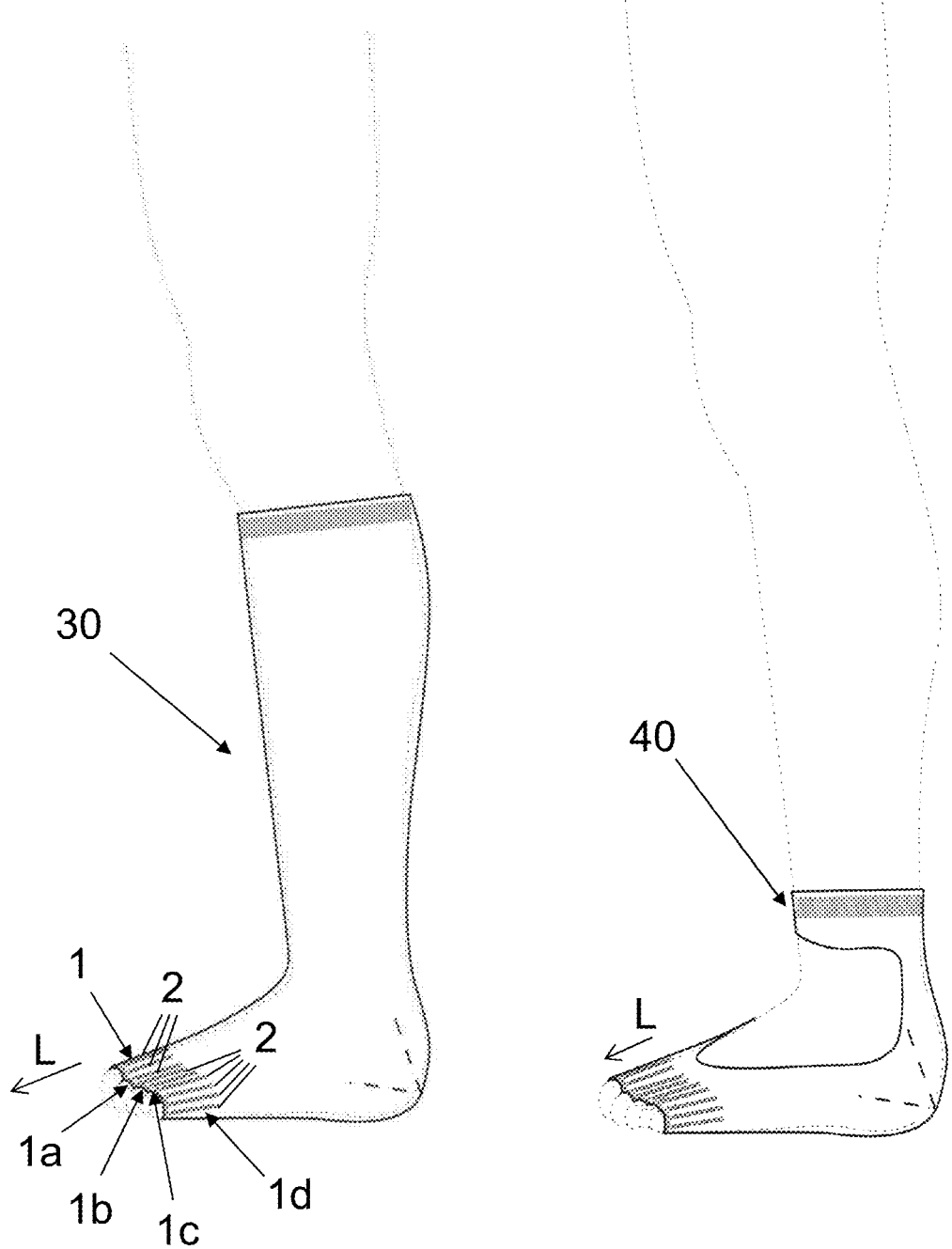
FIGS. 5A and 5B: show a practical example of a compression article according to the disclosure designed as a compression stocking (FIG. 5A) and as liner (FIG. 5B), in which rib-like elevations extend in the longitudinal direction of the corresponding toe receptacle in the area of the toe receptacles of the compression stocking of FIG. 5A and the liner of FIG. 5B.

Compression articles according to the disclosure to be placed on a leg or foot of a wearer are shown in FIGS. 5A and 5B. A compression stocking is shown in FIG. 5A, which can be placed on a lower leg of a wearer. The lower leg compression stocking then has receptacles 1, 1a, 1b, 1c, 1d to accommodate the toes of the wearer. The receptacles 1, 1a-1d are then formed open and contain a cuff at the open end. However, it is also possible to form the toe receptacles 1, 1a-1d closed so that the toes of the wearer can be fully accommodated in the provided receptacle 1, 1a-1d. As in the practical examples of FIGS. 3A and 3B and FIGS. 4A and 4B, in the practical examples depicted in FIGS. 5A and 5B rib-like elevations 2 are also arranged in the area of receptacles 1 for the toes, which extend in the longitudinal direction L of the corresponding receptacle 1 and run parallel to each other across the longitudinal direction at a predetermined spacing d. No elevations 2 are then provided outside the receptacles 1. The practical example depicted in FIG. 5B shows a liner with receptacles 1 to accommodate the toes of the wearer. The liner has a recess in the area of the instep and ankle. This recess can also be omitted so that the foot of the wearer, including the instep and ankle, can be fully enclosed in the form of a sock-like compression article.

It will be readily apparent to one skilled in the art that additional forms of compression articles having at least one receptacle for at least one finger or toe, for example, socks or finger stalls, can be formed according to the disclosure.

What is claimed is:

1. A seamless compression article knitted on a flatbed knitting machine having a front needle bed and a rear needle bed opposite thereto, the compression article including a base structure knitted from at least one weft thread and at least one elastic warp thread inserted or knitted therein, and at least one tubular receptacle adapted to incorporate at least one finger or at least one toe of a wearer of the compression article, wherein the at least one receptacle is extending along a longitudinal direction of the at least one finger or at least one toe of the wearer, when the compression article is placed on a body extremity of the wearer and wherein each of the at least one receptacle includes a plurality of elevations which are formed as ribs and run at least substantially parallel to each other and along the longitudinal direction.

2. The compression article according to claim 1, wherein the base structure has an inner side, which is facing the body extremity when the compression article is placed on the body extremity of the wearer, and an outer side opposite to the inner side, and the base structure is knitted along a wale direction extending at least substantially in the longitudinal direction and has courses running across the wale direction, and the elevations protrude above the base structure on the outer side.

3. The compression article according to claim 1, wherein between 2 and 30 elevations are arranged on each of the at least one receptacle.

4. The compression article according to claim 1, wherein adjacent elevations run parallel and at a predetermined spacing relative to each other, and at least two stitches of the weft thread lie between two consecutive elevations in a course of the base structure.

5. The compression article according to claim 1, wherein a warp thread runs in each or every other course of the base structure.

6. The compression article according to claim 1, wherein the warp thread is incorporated between two consecutive elevations in the direction of courses in each or every other stitch as a tuck loop in the base structure.

7. A seamless compression article including a base structure knitted from at least one weft thread and at least one elastic warp thread inserted or knitted therein, the compression article is comprising at least one tubular receptacle adapted to incorporate at least one finger or at least one toe of a wearer of the compression article, the at least one receptacle is extending along a longitudinal direction of the at least one finger or at least one toe of the wearer, when the compression article is placed on a body extremity of the wearer, and each of the at least one receptacle includes a plurality of elevations which are formed as ribs and run at least substantially parallel to each other and along the longitudinal direction, wherein, in an edge area of the elevations, the warp thread forms two consecutive tuck loops in a course of the base structure.

8. The compression article according to claim 1, wherein the elevations extend in the longitudinal direction of each of the at least one receptacle and at least substantially over the entire extent of the corresponding receptacle and, no elevations are present in the areas of the compression article outside of the at least one receptacle.

9. A seamless compression article including a base structure knitted from at least one weft thread and at least one elastic warp thread inserted or knitted therein, the compression article is comprising at least one tubular receptacle adapted to incorporate at least one finger or at least one toe of a wearer of the compression article, the at least one receptacle is extending along a longitudinal direction of the at least one finger or at least one toe of the wearer, when the compression article is placed on a body extremity of the wearer, and each of the at least one receptacle includes a plurality of elevations which are formed as ribs and run at least substantially parallel to each other and along the longitudinal direction, wherein the elevations are formed by floats and/or tuck loops of the weft thread.

10. The compression article according to claim 1, wherein the base structure is formed from a knit knitted on a flatbed knitting machine with a front layer that is knitted on the front needle bed of the flatbed knitting machine, and a rear layer opposite the front layer and knitted on the rear needle bed of the flatbed knitting machine.

11. A seamless compression article including a base structure knitted from at least one weft thread and at least one elastic warp thread inserted or knitted therein, wherein the base structure is formed from a knit knitted on a flatbed knitting machine with a front layer knitted on a front needle bed of the flatbed knitting machine, and a rear layer opposite the front layer and knitted on the rear needle bed of the flatbed knitting machine, and the compression article is comprising at least one tubular receptacle adapted to incorporate at least one finger or at least one toe of a wearer of the compression article, wherein the at least one receptacle is extending along a longitudinal direction of the at least one finger or at least one toe of the wearer, when the compression article is placed on a body extremity of the wearer, and wherein each of the at least one receptacle includes a plurality of elevations which are formed as ribs and run at least substantially parallel to each other and along the longitudinal direction, wherein the front layer and the rear layer each contain the weft thread and the weft thread forms floats or tuck loops to form the elevations and wherein sites at which the weft thread floats or forms tuck loops are staggered in reversed order by at least one stitch in each consecutive course of the base structure.

12. The compression article according to claim 1, wherein the elastic warp thread is a spandex or rubber thread or a wrapped yarn with a highly elastic core thread that has a thickness in the range of 200 to 1500 dtex.

13. The compression article according to claim 1, wherein the base structure is a right-left knit and/or the base structure is knitted in a 1:1 weave.

14. The compression article according to claim 1, wherein the compression article is a glove and is comprising at least two receptacles, in which one of the receptacles serves to accommodate a thumb and another of the receptacles serves to accommodate at least one finger.

15. A seamless compression article including a base structure knitted from at least one weft thread and at least one elastic warp thread inserted or knitted therein and the compression article is comprising an inner and an outer surface and at least one tubular receptacle adapted to incorporate at least one finger or at least one toe of a wearer of the compression article, wherein the at least one receptacle is extending along a longitudinal direction of the at least one finger or at least one toe of the wearer, when the compression article is placed on a body extremity of the wearer, wherein the base structure has a continuous rib pattern over the outer surface and additionally a plurality of elevations in the area of the at least one receptacle, the elevations protruding above the rib pattern of the base structure and running at least substantially parallel to each other and along the longitudinal direction.

16. The compression article according to claim 9, wherein the elevations in a course of the base structure extend over at least two stitches.

17. The compression article according to claim 1, wherein the elevations in a course of the base structure extend over at least two stitches.

18. The compression article according to claim 1, wherein the compression article comprises pressure-reduced areas, which extend over several consecutive courses in the longitudinal direction and in which no warp threads run.

19. The compression article according to claim 1, wherein the compression article is a stocking having at least two receptacles, in which one of the receptacles serves to accommodate a big toe and another of the receptacles serves to accommodate at least one additional toe.

\* \* \* \* \*